United States Patent
Rohner et al.

(10) Patent No.: US 6,382,967 B1
(45) Date of Patent: May 7, 2002

(54) DENTAL APPARATUS WITH DISPLAY

(75) Inventors: Gottfried Rohner, Alstätten; Bruno Senn, Buchs, both of (CH)

(73) Assignee: Ivoclar AG., Schaan (LI)

( * ) Notice: Subject to any disclaimer, the term of this patent is extended or adjusted under 35 U.S.C. 154(b) by 0 days.

(21) Appl. No.: 09/571,466

(22) Filed: May 16, 2000

(30) Foreign Application Priority Data

Jun. 23, 1999 (DE) .......................... 199 28 805

(51) Int. Cl.⁷ .............................. A61C 1/00; A61C 3/00
(52) U.S. Cl. .......................................... 433/29; 433/27
(58) Field of Search .............................. 433/27, 28, 29, 433/215, 229; 434/263, 264

(56) References Cited

U.S. PATENT DOCUMENTS

| | | | |
|---|---|---|---|
| 4,421,987 A | 12/1983 | Herold | |
| 5,944,531 A | * 8/1999 | Foley et al. | 434/263 |
| 5,961,327 A | * 10/1999 | Lohn | 433/29 X |
| 6,103,203 A | * 8/2000 | Fischer | 433/29 |

FOREIGN PATENT DOCUMENTS

DE    G 80 07 265.7 U1    3/1980

\* cited by examiner

Primary Examiner—Nicholas D. Lucchesi
(74) Attorney, Agent, or Firm—John L. Thompson; Alan S. Korman

(57) ABSTRACT

A dental apparatus has a display and an actuating device for selecting and activating operating programs for operating the dental apparatus. The display has a tooth schematic that is divided into indicator fields. The indicator fields may be distributed over a plurality of teeth so that each indicator field represents one tooth or may be used to indicate certain locations of an individual tooth.

20 Claims, 3 Drawing Sheets

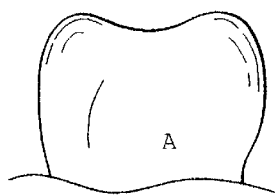
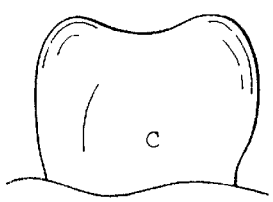
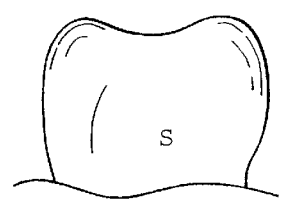
Fig. 8A      Fig. 8B      Fig. 8C
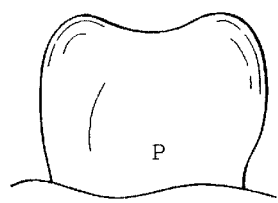
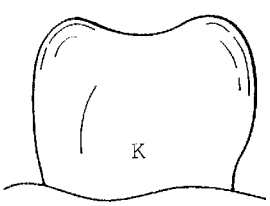
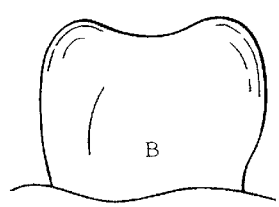
Fig. 9A      Fig. 9B      Fig. 9C
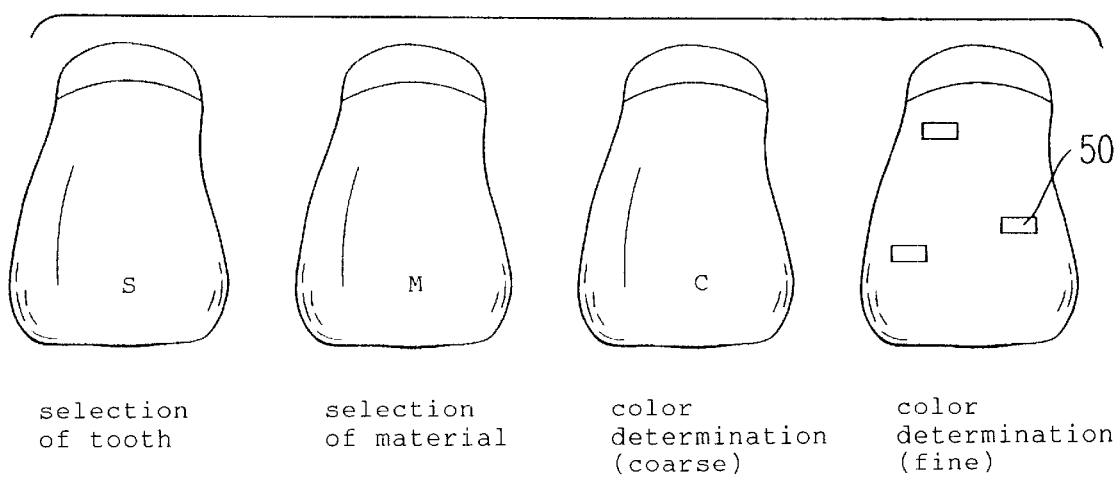
selection of tooth    selection of material    color determination (coarse)    color determination (fine)
Fig. 10

DENTAL APPARATUS WITH DISPLAY

BACKGROUND OF THE INVENTION

The present invention relates to a dental apparatus comprising a display and an actuating device by which at least two programs for the dental apparatus can be selected and actuated.

Such dental apparatus have been known for some time. Dental apparatus can be realized for different applications. For example, a dental apparatus can be embodied as a mixing device or as a firing furnace. In all cases, a program-controlled operation is provided. In the simplest case, for example, for a mixing device, the substances to be mixed are introduced and a starting key is pressed for actuating the mixing process. It is known to indicate the operational mode of such dental apparatus via displays which, in the simplest case, are operation-indicating lights but can also be in more complex forms.

A dental apparatus embodied as a light-curing device which is provided with a display and also has an actuating device, is known, for example, from DE-GM 80 072 657. In this device the display is a numerical display of saved values of a time counter. Such a display can provide information to the dentist or dental technician with respect to the advancement of the curing process of the dental apparatus. However, they do not provide any further detailed information which is not critical only when the dental technician or dentist concentrate on the curing process during the curing step so that the operator knows exactly which type of restoration is to be carried out and which one of the programs is being used.

Furthermore, it has been suggested to provide a dental apparatus with different programs which, depending on the application, provide different light curing curves.

Light curing curves can differ with respect to the course of the starting curve, with respect to the maximum light intensity, but also with respect to whether an intermediate or pulsed operation or continuous operation is to be performed whereby for intermediate operation the frequency and signal shape of the emitted light can also differ.

It was shown by tests, that depending on the location of application different light curing curves are beneficial. When, for example, inner linings or small fillings must be polymerized, the use of maximum output carries the risk that, due to the increased shrinking force, open margins will result. This means that for small size fillings it is necessary to perform curing at lower light output even though this light output would be insufficient with respect to curing respectively larger sized fillings or crowns. For large sized fillings or crowns which may also optionally have very complex shapes, it was found to be beneficial to employ a pulsating operating mode.

On the other hand, there is the risk that the operator for the dental apparatus is overtaxed, when for the curing process first a preliminary examination with respect to the curing problem must be performed and, subsequently, an optionally only numerically specified program must be selected.

The operation of the device also entails the risk that the dentist or dental technician, especially during the hectic work situation of a dental clinic, will accidentally switch the number of the selected curing program and, despite an optimized and specified theoretically determined value, the wrong curing action is performed so that either open margins are observed or the filling is not completely cured.

It is therefore an object of the invention to provide a dental apparatus of the aforementioned kind which can be more easily adapted to the work situation in a dental clinic and which is easy to operate.

SUMMARY OF THE INVENTION

This object is solved in that the display has at least one tooth schematic, especially with a plurality of fields.

The invention will be disclosed in the following, using as an example a light-curing device, whereby it is understood that other types of dental devices can be used in connection with the present invention.

Inventively, it is especially favorable to have an optimal correlation between the location of treatment and the operating program. The dentist to operate the inventive device no longer has to deal with numerically identified programs when the inventive display is used because he or she can select in a very short period of time the required treatment symbol by simply repeatedly actuating the actuating key of the actuating device until the corresponding image or pictogram appears.

It is especially favorable that the inventive light-curing device is realized with a display employing liquid crystal technology. This allows to display different areas of a tooth to be restored so that it is, for example, possible to show the light-curing lining, the light-curing adhesives, the crowns, the bridges, the inlays or composites to be cured, whereby, depending upon the selection of the corresponding operating or indicator field, the corresponding program is activated. The respective indicator fields on the display are preferably embodied in the shape of a stylized tooth whereby it is understood that, if necessary, additional or auxiliary information can be provided. When employing a liquid crystal display, it is possible to alternatingly switch the respective field and synchronously activate the corresponding program or operational mode.

It is especially advantageous that operation can be carried out interactively by a single key control. For example, the operator before actuating the light curing device can simply repeatedly press the actuating key for selecting the desired operational mode in a cyclical manner, whereby for the operational mode the corresponding location of treatment is displayed on the display in a manner such that a selection option is signaled, for example, by blinking of the corresponding indicator field.

As soon as the corresponding operational mode and the location of treatment have been activated in this manner, the operator can then start the polymerization process by actuating the actuator key differently, for example, by pressing twice with a very short interval, the so-called double clicking, or by holding down the actuator key for an extended time period. This is also indicated on a corresponding display, for example, by additionally activating a corresponding indicator field on the display or by continuously displaying the indicator field for the application or treatment location.

In a preferred embodiment, it is instead suggested that preselection is indicated by blinking or continuous activation of the respective restoration field or by operating the corresponding field with reduced display intensity. Certain crystal displays allow such a mode of operation. In modified embodiments it is suggested to then operate during operation of the dental apparatus the corresponding display field with maximum intensity.

Inventively, the transfer of the programming information into the location information is especially important whereby the corresponding program for the dental apparatus is preset such that action by the operator is no longer required or even desired. Accordingly, the operating safety is considerably increased. The error probability for operation of the device is accordingly also reduced.

It is understood that, if necessary, additional fields can be provided within the display unit. Especially a bar display is of particular use which symbolically represents the intensity of the light output of the light source in an easily comprehensible manner. Such a bar display is suitable also as an indicator for activity, i.e., for the operating time of the light-curing device. Furthermore, it is also possible to provide alpha-numerical fields which, because of the minimal amount of space available, are preferably used to display abbreviations or alpha-numerical codes for indicating the operation mode. For example, the operational mode "low power", "pulse program", as well as "high power", can be respectively indicated as "LOP", "PUL", and "HIP".

BRIEF DESCRIPTION OF THE DRAWINGS

The object and advantages of the present invention will appear more clearly from the following specification in conjunction with accompanying drawings, in which:

FIGS. 8a, 8b, and 8c show three representations of a display for a dental mixing device in a symbolized manner;

FIGS. 9a, 9b, and 9c show three representations of a display for a firing furnace in a symbolized form; and FIG. 10 shows a schematic representation of a further embodiment of a dental apparatus, i.e., a color determining device, with representation of the display in different stages.

DESCRIPTION OF PREFERRED EMBODIMENTS

The present invention will now be described in detail with the aid of several specific embodiments utilizing FIGS. 1 through 10.

Figure 1:
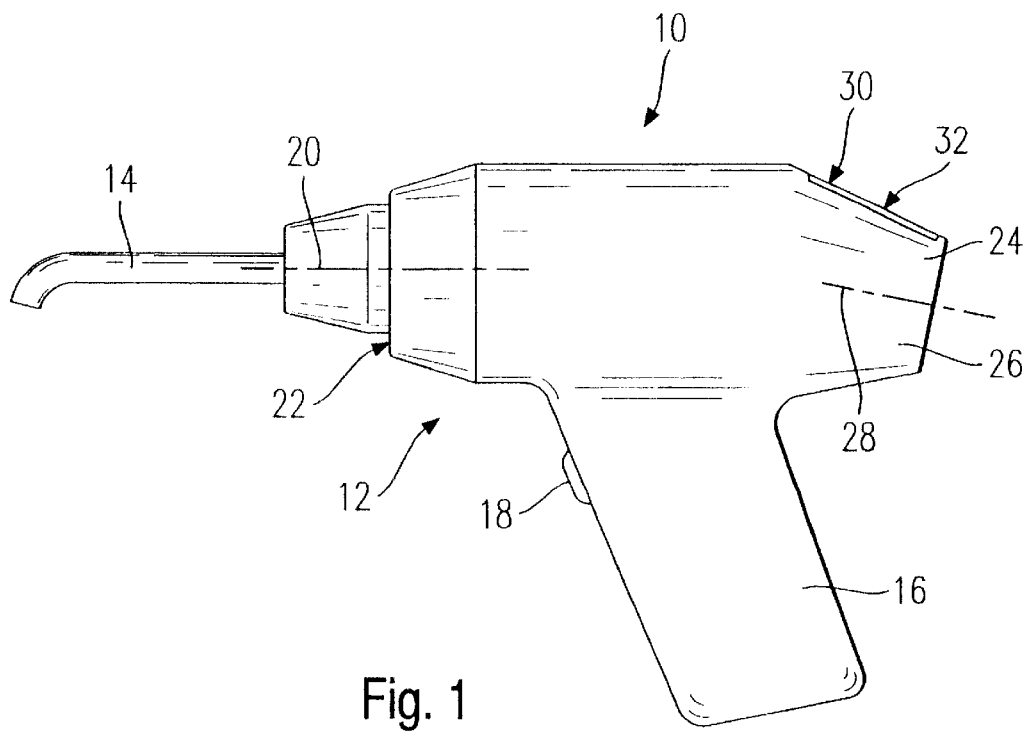
FIG. 1 shows a side view of an inventive light-curing device.

Dental device 10 represented in FIG. 1 comprises a hand-held device 12 which is either battery-operated and accordingly provided with electrical energy by a charging station, when not in operation, or is connected by a flexible current supply cable to a base station. The hand-held device 12 is substantially pistol-shaped whereby the forward end ("gun barrel") is provided by a light guide rod 14 that at its free end is curved. A grip 16 of the hand-held device 12 has an actuator key 18 as a part of a non-represented actuating device. The actuating device is used to select and to actuate various programs as desired.

The dental apparatus 10 has a high output halogen lamp which has a light outlet along the optical axis 20. The optical axis 20 extends parallel to the light guide rod 14 and substantially aligned with the housing axis of the upper portion of the hand-held device 12.

Since known halogen lamps, in addition to emitting light of high intensity, also emit heat, it is expedient and necessary to provide the hand-held device 12 with a blower cooling device. For this purpose, cooling channels extend through the upper portion of the hand-held device 12, in a direction from an air inlet 22 to the rear. The cooling channels extend as close as possible to the halogen lamp. In the rearward portion 24 an axial blower is provided, and the cooling air exits the hand-held device 12 through air outlet 26. The air outlet 26 extends inventively preferably along an axis 28 which is angled relative to the axis 20 in a downward direction. This embodiment has the advantage that at a slanted upper or top side 30 of the rearward portion 24 space for the inventive display 32 is provided. At the same time, the air stream exiting from the device will not directly flow onto the dentist or dental technician but instead in a slanted direction downwardly. Also the display 32 in this arrangement is positioned advantageously with respect to the field of view of the dentist.

It is understood that the angle between the axes 20 and 28 can be adjusted within a wide range to the respective specifications but can also be adapted with respect to aesthetic designs of the dental apparatus. In the shown embodiment the angle is 15°, and this angle practically completely avoids flow losses which could result from an angled arrangement.

In the shown embodiment the top side 30 and the arrangement of the display 32 are positioned downward slant angle of 25° to the rear relative to the optical axis 20. It is understood that this angle is also matched to the specifications whereby it is taken into consideration that for an embodiment of the display 32 with liquid crystal technology the known liquid crystal displays can be adjusted such that the maximum contrast is provided for a reading angle which is different from 90°.

It is understood that the inventive display is not limited to liquid crystal technology. For example, plasma displays are also useful, and LED displays or any other suitable display technology can be used whereby preferably a field arrangement of the individual display fields is preset. Display fields can, of course, also be arranged as a matrix of individual indicator points.

The display unit 32 is preferably somewhat recessed with respect to the top side 30, as is represented schematically in FIG. 1. With known technologies it is also possible to adapt the readability of the display to the respective requirements whereby the recessed arrangement provides an improved protection of the display even under rough handing conditions of the hand-held device 12.

Figure 2:
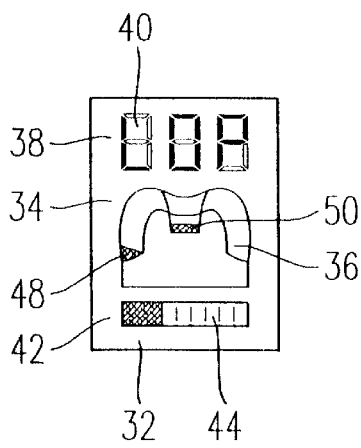
FIG. 2 shows a view of the display for the dental apparatus according to FIG. 1.

FIG. 2 shows the indicator and/or display fields of the display 32 of the shown embodiments. The display 32 is preferably of an upright rectangular shape with a height/width ratio of approximately 3 to 2 so that it can be fitted easily onto the top side 30. The display 32 is flat for reasons of an inexpensive manufacture, while the upper side 30 is rounded in order to complement the substantially cylindrical shape of the upper portion of the hand-held device 12.

The display 32 has preferably three areas. The middle portion 34 is comprised of a stylized tooth 36 with different individual indicator fields. An upper portion 38 provides a three digit seven-bar display 40. A lower portion 42 provides a bar display 44.

The stylized tooth has different fields. In FIG. 2 dark indicator fields symbolize class 5 of tooth neck fillings 48 as well as linings 50. In the operational mode indicated in FIG. 2, inner linings and/or class 5 tooth neck fillings are to be cured. The seven-bar display LOP shows low power operation, i.e., a minimal energy supply, useful for curing inner linings and/or class 5 tooth neck fillings.

Additionally, the bar display is excited in the left area while it is in a rest position in the right area. This means that only a small amount of the entire energy output is currently in use.

The display according to FIG. 2 symbolizes the operational state of selecting the program for light-curing of inner linings and class 5 tooth neck fillings, i.e., the state before the program is actually activated. The actual activation of the program is carried out by a corresponding actuation of the actuating device.

In the shown embodiment it is suggested that the three programs LOP, PUL, and HIP, are sequentially switched by continuous pressure onto the actuating key 18. When releasing the actuating key 18, the selected programs, are activated. The switching is carried out in cycles so that the program LOP will again follow the program HIP.

According to a modified embodiment, it is suggested that the initiated change between the operational modes is carried out by a one time actuation and release of the actuating key 18 and that the activation of the respectively selected program is carried out by a longer extended actuation of the actuating key 18, for example, for a time period of more than one second.

Figure 3:
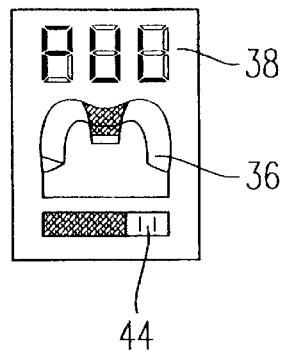
FIG. 3 is a view of the display according to FIG. 2, whereby another mode of operation is illustrated.

FIG. 3 shows in which manner the fields of the stylized tooth 36 can be activated by a pulsed operational mode. In this operational mode, the indicator field for large fillings is active whereby this activation coincides with suitability of a pulsating operational mode especially for large fillings. The bar display 44 is activated in a central area in order to indicate the medium output as a result of integration over time. Alternatively, a bar display which changes with regard to excitation can also represent the pulsating operational mode. The upper portion 38 shows the letters PUL which also indicate the respective operational mode.

Figure 4:
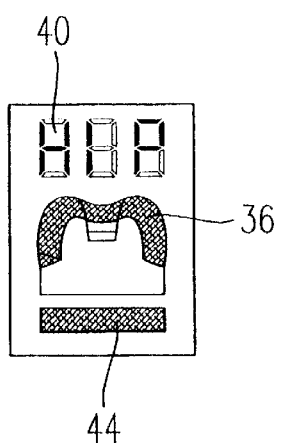
FIG. 4 shows a view of the display according to FIG. 2 whereby another mode of operation is illustrated.

FIG. 4 shows in the area of the stylized tooth 36 an activation field for cementing large crowns, while the bar display 44 is shown fully activated. The seven bar or seven segment display 40 shows HIP which indicates high power, i.e., high output.

When comparing FIGS. 3 and 4, it is clear that in the operational mode according to FIG. 4 the fields of the middle portion 34, which in the operational mode according to FIG. 3 or FIG. 2 are activated, are now also activated. It is essential that the dentist or the dental technician can detect on the represented stylized tooth immediately the suitability of the respective operational mode for the light-curing task.

Figures 5, 6, 7:
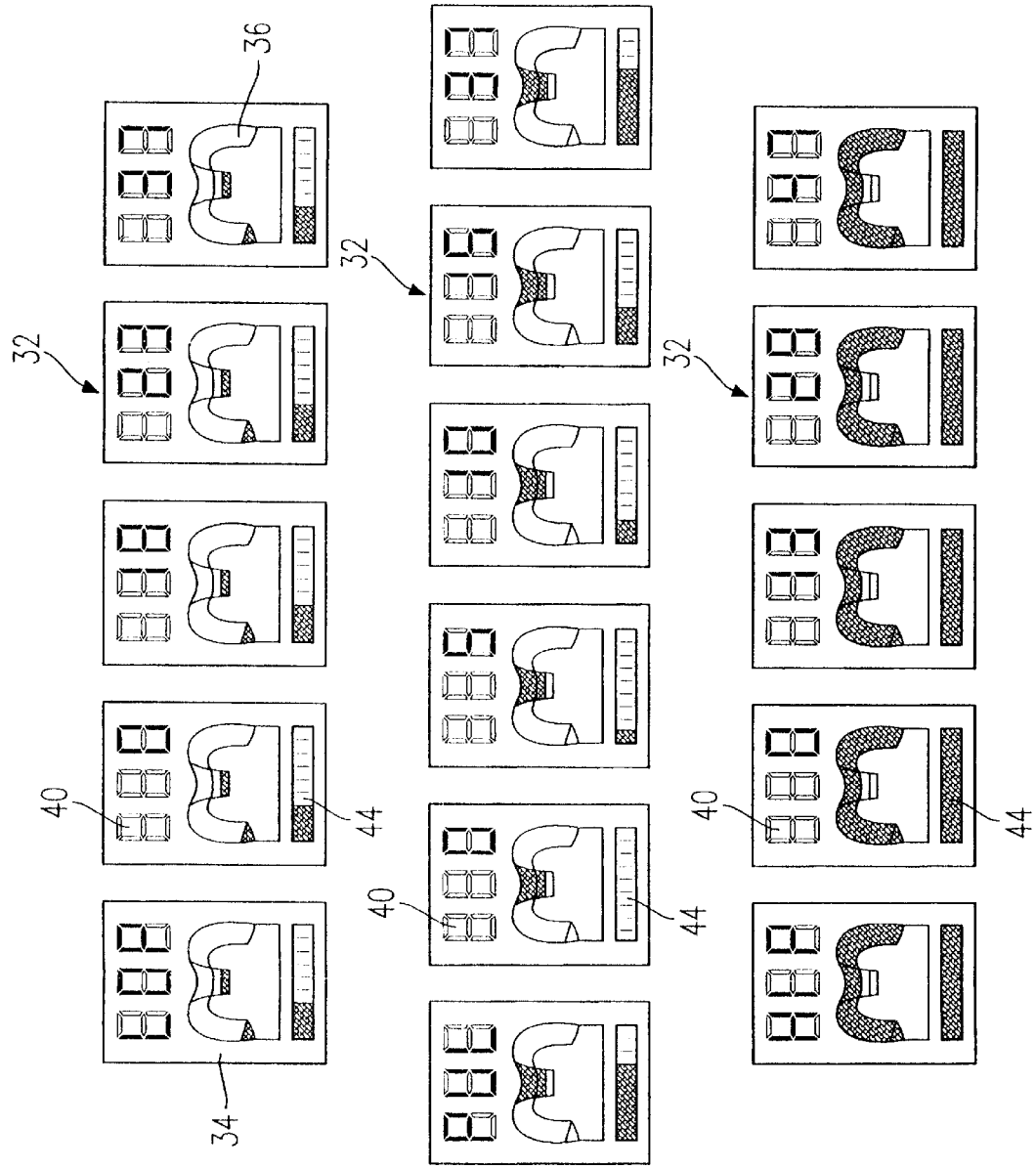
FIG. 5 is a view of the display according to FIG. 2 whereby different points in time during the light curing process are represented in sequence.
FIG. 6 shows a view of the display according to FIG. 3 whereby in sequence different points of time during a light curing process are represented.
FIG. 7 shows a view of the display according to FIG. 4 whereby in sequence different points in time during the light curing process are represented.

FIGS. 6 and 7 show respectively the course of the respective operational mode as a function of time. FIG. 5 shows the display 32 at five different points in time, and the representation all the way to the left shows the preparation of the corresponding operational mode, corresponding to FIG. 2. The second representation from the left shows the point in time directly after switching on of the program LOP. The seven bar display 40 changes from LOP to zero, which indicates that at this point in time zero seconds of the light curing process have been past. The bar display 44 remains in its initial position which is also true for the middle portion 34 with the stylized tooth 36.

During the light curing process only the seven segment display 40 will change over the course of time represented by the illustrated seconds 18, 23 and 37, while at the end of the light curing process the display will shut down in order to signalize to the dentist the completion of the light-curing process.

In the same manner, the light-curing device for the pulse operation is represented in FIG. 6. The representation farthest to the left corresponds to FIG. 3 and the second representation from the left corresponds to the state upon actuating of the actuation key 18 for the selected operational mode. The activated portion of the bar display 44 is in this mode of operation initially very small, corresponding to the intensity of the emitted light. The pulse intensity increases with the program PUL over the light-curing duration, which is represented accordingly for the different points in time 5 seconds, 10 seconds, 15 seconds, and 37 seconds in FIG. 6.

It is understood that a pulsating bar display can also be provided in order to indicate the pulse program also during the light curing process, whereby the liquid crystal displays known presently allow a display frequency of slightly less than one second.

In FIG. 7 a light-curing process for a program selection HIP according to FIG. 4 is represented in an analog manner. The representation all the way to the left shows the selection of the display device 32 at the point in time before the light-curing program is selected. The second representation shows the display unit 32 directly at the start upon actuation of the actuating key 18 whereby the bar display 44 is completely excited and the seven bar display 40 is zero. The program HIP lasts 47 seconds so that the representation all the way to the right shows the time 47 seconds on the seven bar display 40.

It is understood that the provided display images are only exemplary and can be changed as desired and as needed according to the specific requirements.

FIG. 8A through FIG. 8C show a further embodiment of the inventive dental apparatus. It is a mixing device that has a display in the form of a tooth so that it is already optically indicated what the purpose of the device is. The display is switched with corresponding display fields whereby the letters A, C, and S represent the use of amalgam in the mixing device, of composite, and the use of a mixing syringe, respectively.

FIGS. 9A through 9C show a display unit for a firing furnace as a further embodiment of the dental apparatus whereby in this case a tooth schematic is also symbolically shown. Different operational modes or output stages of the firing furnace can be represented with corresponding symbolic display contents, whereby P is provided to indicate program selection, K is provided for selecting firing of a crown, and B is selected for firing of a bridge.

FIG. 10 shows a coloring measuring device as a dental apparatus whereby only the corresponding display unit is schematically shown Four different display contents are provided, i.e., S for tooth selection, M for material selection, C for color determination (coarse) as well as a schematic with individual display fields 50 on the schematic tooth field which indicate color determination (fine).

It is understood that the corresponding inventive displays can also be used in connection with other dental devices. For example, a ceramic pressing furnace, a preheating furnace, a metering device, a computer program for a dental device, a deep drawing device, a copying milling device, a pressure polymerization apparatus, and further devices can be provided with the inventive display.

The present invention is, of course, in no way restricted to the specific disclosure of the specification and drawings, but also encompasses any modifications within the scope of the appended claims.

What is claimed is:

1. A dental apparatus (10) comprising:
   a display (32);
   an actuating device (18) for selecting and activating operating programs for operating said dental apparatus;
   said display (32) comprising a tooth schematic (36).

2. A dental apparatus according to claim 1, wherein said tooth schematic (36) is divided into indicator fields.

3. A dental apparatus according to claim 2, wherein said indicator fields are distributed over a plurality of teeth.

4. A dental apparatus according to claim 3, wherein each one of said indicator fields represents a tooth.

5. A dental apparatus according to claim 2, wherein said indicator fields match an application location of the tooth for which said programs are suitable.

6. A dental apparatus according to claim 2, wherein said actuating device comprises an actuating key (18) and wherein the operating program is selected by repeatedly pressing said actuating key (18) until the desired operating program is displayed as a respective symbol in one of said indicator fields and is activated.

7. A dental apparatus according to claim 2, wherein said actuating device displays sequentially operating programs and/or application locations and allows a sequential selection of the operating programs and/or application locations and wherein activation of said dental apparatus is also performed by said actuating device.

8. A dental apparatus according to claim 2, comprising a light-curing device, wherein the operating programs are light-curing programs.

9. A dental apparatus according to claim 8, wherein said light-curing device is a hand-held device.

10. A dental apparatus according to claim 8, wherein an operating program activates an indicator field of the tooth schematic that shows an application suitable for the selected operating program.

11. A dental apparatus according to claim 8, wherein said display (32) further comprises auxiliary fields (40) indicating an operational mode of said dental apparatus, wherein said auxiliary fields (40) are numerical fields displaying curing duration and/or remaining curing duration.

12. A dental apparatus according to claim 8, wherein said display (32) comprises at least one display field (44) for a light intensity of said light-curing device.

13. A dental apparatus according to claim 12, wherein said display field (44) is a bar indicator.

14. A dental apparatus according to claim 8, wherein said display (32) is arranged at a rearward surface (30) of said light-curing device (12) and is positioned within a field of view of a dentist operating said dental apparatus.

15. A dental apparatus according to claim 8, wherein a pulsed operational mode of said light-curing device (12) is signaled by a clock-controlled display field.

16. A dental apparatus according to claim 1, wherein said indicator fields are symbolic application locations.

17. A dental apparatus according to claim 1, wherein said display (32) further comprises auxiliary fields (40) indicating an operational mode of said dental apparatus.

18. A dental apparatus according to claim 17, wherein said auxiliary fields (40) show an alpha-numerical code to indicate the operational mode.

19. A dental apparatus according to claim 1, wherein said auxiliary fields (40) have multiple display functions.

20. A dental apparatus according to claim 19, wherein said auxiliary fields (40) display an operating period.

* * * * *